(12) United States Patent
Ingram et al.

(10) Patent No.: US 6,333,181 B1
(45) Date of Patent: *Dec. 25, 2001

(54) ETHANOL PRODUCTION FROM LIGNOCELLULOSE

(75) Inventors: Lonnie O. Ingram; Brent E. Wood, both of Gainesville, FL (US)

(73) Assignee: University of Florida Research Foundation, Inc., Gainesville, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/833,435

(22) Filed: Apr. 7, 1997

(51) Int. Cl.$^7$ ............................................ C12P 7/10
(52) U.S. Cl. ..................... 435/165; 435/163; 435/170; 435/72; 435/99; 435/173.2; 435/173.8; 435/277; 435/278
(58) Field of Search ............................ 435/99, 165, 163, 435/278, 277, 170, 72, 173.2, 173.8

(56) References Cited

U.S. PATENT DOCUMENTS

| | | |
|---|---|---|
| 5,000,000 | 3/1991 | Ingram et al. . |
| 5,028,539 | 7/1991 | Ingram et al. . |
| 5,424,202 | 6/1995 | Ingram et al. . |
| 5,482,846 | 1/1996 | Ingram et al. . |
| 5,487,989 | 1/1996 | Fowler et al. . |
| 5,514,583 | 5/1996 | Picataggio et al. . |
| 5,554,520 | 9/1996 | Fowler et al. . |
| 5,602,030 | 2/1997 | Ingram et al. . |

FOREIGN PATENT DOCUMENTS

WO95/13362   8/1994   (WO) .

OTHER PUBLICATIONS

Nakao et al, Ann. N.Y. Acad. Sci. 613 (Enzyme Engineering 10) pp. 802–807. 1990.*

Allison, D.G., et al., "The effect of ultrasound on *Escherichia coli* viability" 1996. *J. Basic Microbiol.* 36(1):3–11.

Atchley, A.A., and L.A. Crum. "Chapter 1: Acoustic cavitation and bubble dynamics" *Ultrasound: Its Chemical, Physical, and Biological Effects.* K.S. Suslick ed. VCH, New York, N.Y. 1988.

Boudjouk, P. "Chapter 5. Heterogeneous sonochemistry" *Ultrasound: Its Chemical, Physical, and Biological Effects.* K.S. Suslick ed. VCH, New York, N.Y. 1988.

Brooks, T.A. and L.O. Ingram. "Conversion of mixed office paper to ethanol by genetically engineered *Klebsiella oxytoca* strain P2" 1995. *Biotechnol. Prog.* 11(6):619–625.

Kaya, F., J.A. Heitmann, Jr., and T.W. Joyce. "Cellulase binding to cellulose fibers in high shear fields" 1994. *J. Biotech.* 36:1–10.

Nazhad, M.M., L.P. Ramos, L. Paszner, and J.N. Sadler. "Structural constraints affecting the initial enzymatic hydrolysis of recycled paper" 1995. *Enz. Microb. Tech.* 17:68–74.

Norman, J.C., N.J. Sell, and M. Danelski. "Deinking laser-print paper using ultrasound" 1994. *TAPPI J.* 77:151–158.

Scott, W.E. and P. Gerber. "Using ultrasound to deink xerographic waste" 1995. *TAPPI J.* 78:125–130.

Sell, N.J., J.C. Norman, and D. Jayaprakash. "Deinking secondary fiber using ultrasound" 1995. *Progress in Paper Recycling.* Aug. p.28–34.

Suslick, K.S. "Chapter 4. Homogeneous sonochemistry" *Ultrasound:Its Chemical, Physical, and Biological Effects.* K.S. Suslick ed. VCH, New York, N.Y. 1988. 123–146.

Suslick, K.S. "Sonochemistry" 1990. *Science.* 247:1439–1441.

Shoh, A. "Chapter 3. Industrial applications of ultrasound" *Ultrasound:Its Chemical, Physical, and Biological Effects.* K.S. Suslick ed. VCH, New York, N.Y. 1988.

Suslick, K.S. "The Chemical Effects of Ultrasound" 1989. *Scientific American.* Feb. p. 80–86.

Volmer, A.C., I.R.S. Maken and E.C. Everbach. "Induction of the heat shock response in *Escherichia coli* by the effects of acoustic cavitation from Ultrasound" Abstr. I–85, p. 317. Abstr. 96th Annu. Meet. Am. Soc. Microbiol. American Society for Microbiology, Washington D.C. 1996.

Wang, D., M. Sakakibara, N. Kaoyuki, K. Suzuki. "Ultrasound enhanced lactose hydrolysis in milk fermentation with *Lactobacillus bulgaricus*"1996. *J. Chem Tech. Biotechnol.* 65:86–92.

Rolz, C., "Regulation of adsorption–desorption mechanisms during holocellulosis of biomass", *Trends in Biotech.*, 4(6):135–136 (1986).

Rolz, C., "Ultrasound Effect of Enzymatic Saccharification", *Biotech. Letters*, 8(2):131–136 (1986).

Gama, F.M. et al., "Comparative study of cellulose fragmentation by enzymes and ultrasound," *Enzyme and Microbial Technology* 20:12–17 (1997).

Tetsuo, Koshijima, "Recovering Method for Cellulase," *Agency of Ind Science & Technol 012(209)* Abstract (Jun. 15, 1988).

Kondakov, A.F. et al., Database WPI, Sechtion Ch, Week 8045 1980/Derwent Publications Ltd., London, GB XP002071671 & SU 724 567 A (Ferment Products) Abstract.

(List continued on next page.)

Primary Examiner—Francisco Prats
(74) Attorney, Agent, or Firm—Lahive & Cockfield; Peter C. Lauro, Esq.

(57) ABSTRACT

This invention presents a method of improving enzymatic degradation of lignocellulose, as in the production of ethanol from lignocellulosic material, through the use of ultrasonic treatment. The invention shows that ultrasonic treatment reduces cellulase requirements by ⅓ to ½. With the cost of enzymes being a major problem in the cost-effective production of ethanol from lignocellulosic material, this invention presents a significant improvement over presently available methods.

16 Claims, 2 Drawing Sheets

OTHER PUBLICATIONS

Wood, B.E. et al., "Ultrasound Stimulates Ethanol Production during the Simultaneous Saccharification and Fermentation of Mixed Waste Office Paper," *Biotechnol. Prog.* 13:232–237 (1997).

Barton, Stephen et al., "The effects of ultrasound on the activities of some glycosidase enzymes of industrial importance," *Enzyme and Microbial Technology* 18:190–194 (1996).

Dolganova, N et al. "Ultrasonic Stimulation of Chlorella Population Growth" *Acta Ichthyologica et Piscatoria* 24(2):165–170 (1994).

Earnshaw, R.G. et al. "Understanding Physical Inactivation Processes Combined Preservation Opportunities Using Heat, Ultrasound and Pressure" *International Journal of Food Microbiology* 28:197–219 (1995).

Idnssi, F.Z. et al. "Effect of Ultrasound on Fungal Cells" *Cytobios* 88:119–122 (1996).

Moncan, T. et al. "Use of Ultrasound to Increase Infection of McCoy Cell Monolayers by *Chlamydia trachomatis* Strain" *Biologicals* 19:53–55 (1991).

Scherba, G. et al. "Quantitative Assessment of the Germicidal Efficacy of Ultrasonic Energy" *Applied and Environmental Microbiology* 57(7) 2079–2084 (Jul. 1991).

Thomas, B.J. et al. "Effect of Low–Dose Ultrasonic Treatment on Growth Rates and Biomass Yield of *Anabaena flos aquae* and *Selenastrum capricornutium*" *Biotechnology Techniques* 3(6):389–392 (1989).

Tiehm, A. et al. "The Use of Ultrasound to Accelerate the Anaerobic Digestion of Sewage Sludge" *War. Sci. Tech.* 36(11) 121–128 (1997).

Velji, M.I. and Albright, L.J. "Microscopic Enumeration of Attached Marine Bacteria of Seawater, Marine Sediment, Fecal Matter, and Kelp Blade Samples Following Pyrophosphate and Ultrasound Treatments" *Can. J. Microbiol.* 32:121–126 (1986).

Brau, B. et al., (1986) "Cloning and Expression of the Structural Gene for Pyruvate Decarboxylase of *Zymomonas mobilis* in *Escherichia coli*," Arch. Microbiol. 144:296–301.

Curry, C. et al, "Expression and Secretion of a *Cellulomonas fimi* Exoglucanase in *Saccharomyces cerevisiae*", Appl. Environ. Microbiol., Feb. 1988, vol. 54, No. 2, pp. 476–484.

Grepinet, O. et al., (1988) "Purification of *Clostridium thermocellum* Xylanase 2 Expressed in *Escherichia coli* and Indietificationof the Corresponding Product in the Culture Medium of *C. thermocellum*," J. Bacteriol. 170:4576–4581.

Ingram, L. O. et al., "Genetic engineering of ethanol production in *Escherichia coli*," Appl. and Environ. Microbiol., 53:2420–2425 (1987).

Joliff, G. et al., "Isolation, Crystallization and Properties of a New Cellulase of *Clostridium thermocellum* Overproduced in *Escherichia coli*" Bio/Technology, vol. 4, Oct. 1986, pp. 896–890.

Neale, A. D. et al. (1987) "Nucleotide Sequence of the Pyruvate Decarboxylase Gene from *Zymomonas mobilis*," Nucleic Acids Res. 15:1753–1761.

Tolan, J. S. and R. K. Finn (1987) "Fermentation of D–Xylose and L–Arabinos to Ethanol by *Erwinia chrysanthemi*," Appl. Environ. Microbiol. 53:2033–2038.

Tolan, J. S. and R. K. Finn (1987) "Fermentation of D–Xylose to Ethanol by Genetically Modified *Klebsiella planticola*," Appl. Environ. Microbiol. 53:2039–2044.

* cited by examiner

US 6,333,181 B1

ETHANOL PRODUCTION FROM LIGNOCELLULOSE

GOVERNMENT FUNDING

This invention was made, in part, with support by grants from the United States Department of Agriculture (95-37308-1843), the United States Department of Agriculture Cooperative Research Agreement (3620-41000-051-02S), the United States Department of Energy (DE-FG05-86ER13574) and the University of Florida. The government may have certain rights in the application.

BACKGROUND OF THE INVENTION

Ultrasound can be defined as sound waves above the range of human perception (Price, 1992). Currently, many ultrasonic technologies such as SONAR, medical diagnostics, and surface cleaners are available. SONAR and medical applications typically use low power and high frequency ($\geq 1$ MHz). Surface cleaning applications, however, depend on ultrasonic cavitations created by lower frequency (20–50 Khz) and high power ultrasound.

Ultrasonic cavitations result from the rapid compression and expansion of a liquid. In the expansion phase, the liquid is "torn apart", resulting in the formation of voids or bubbles (Price, 1992; Leeman and Vaughan, 1992). These bubbles gradually increase in size until a critical size is reached, where critical size (usually 100–200 $\mu$m in diameter) is dependent on the frequency of the oscillation and the presence of any nucleating agents, e.g., dissolved gasses, cracks and crevices on a solid surface, or suspended solids (Atchley and Crum, 1988; Price, 1992). Once its critical size is reached, the bubble implodes, at times, generating temperatures approaching 5,500° C. within the bubble (Suslick, 1989, Price, 1992). When collapse of a cavity occurs in a solution free of solid particles, heating is the only consequence. However, if implosion occurs near a solid surface, implosion is asymmetric. As water rushes to fill the void left by the imploding bubble (e.g., at speeds near 400 m/s) shock pressures of 1–5 Kpa can be generated (Suslick, 1988; Suslick, 1989; Price, 1992).

The physical effects of ultrasonic cavitations have been known since the early testing of the first British destroyer, the H.M.S. Daring, in 1894 (Suslick, 1990). The rapid revolution of a ship propeller creates the same, high frequency, compressions and expansions created by ultrasound (Suslick, 1989). Cavitations around the Daring's propeller caused pitting of the metals used. This effect of cavitations on metal surfaces has been confirmed in studies on ultrasonic cavitations (Leeman and Vaughan, 1992; Boudjouk, 1988). High intensity stirring, the dispersal of suspended solids, increased diffusion through cellulose gels, and emulsification of immiscible liquids are other effects attributable to ultrasonic cavitations (Ensminger, 1973).

The high temperatures, pressures and velocities produced by ultrasonic cavitation can also create unusual chemical environments (Suslick, 1989). Compounds in aqueous solution have been shown to form free radicals when subjected to ultrasound. Water, when subjected to ultrasound, creates H. and .OH intermediates, ultimately producing $H_2$ and $H_2O_2$ (Suslick, 1988). Other chemical effects can be caused by high velocity collisions driven by shock waves. The agglomeration of metallic particles in ultrasonic fields has been shown (Suslick, 1989; Suslick, 1990).

Ultrasonic surface cleaners have been available for use since the early 1950's (Shoh, 1988). The mechanism of the cleaning action is reliant on the formation of cavitation bubbles. The contaminant coat can be gradually eroded through cavitational action. Alternatively, the formation of cavitational bubbles between the coat and the surface, effectively peels the coat away from the surface. Other designs of ultrasonic cleaning systems have extremely high efficiency (>95%).

Most biological applications of ultrasonic technology have been directed towards the disruption of cell membranes (Shoh, 1988; Ausubel, 1996). One such device is Fisher Scientific's Model 550 Sonic Dismembrator. Recently, the effects of lower intensities of ultrasound on bacteria have been investigated. It has been shown that nonlethal doses of ultrasound may cause the induction of the SOS response and the transcription of heat shock proteins in *Escherichia coli* (Volmer et al., 1996). Some of the physical damage to *E. coli*, by ultrasonic cavitation, has been illustrated recently (Allison et al., 1996), showing the disruption of the plasma membrane and subsequent leakage of intracellular components.

In the fermentation of milk by *Lactobacillus bulgaricus*, the rate of lactose hydrolysis was increased with the use of discontinuous ultrasound (Wang et al., 1996). Presumably, the cause of the increased rate of hydrolysis was the release of intracellular enzymes into the media. After ultrasonic treatment was stopped, *L. bulgaricus* was able to recover and grow.

Recent interest in ultrasound has been shown by those involved in research in the paper industry investigating its uses as a de-inking device in the recycling of various office paper (Scott and Gerber, 1995; Sell et al., 1995; Norman et al., 1994). It was reported that, because of ultrasonic treatment, the structure of the paper was changed such that its water holding capacity increased.

Besides the recycling of paper products, there is an interest in the fermentation of waste paper and other lignocellulosic products into ethanol. The production of ethanol from such products reduces environmental waste problems and reduces reliance on petroleum-based automotive fuels. (Hohmann and Rendleman, 1993; Sheehan, 1993). Accessibility of the substrate to cellulase is a primary factor influencing the efficiency of enzymatic degradation of cellulose (Nazhad et al., 1995).

Cellulase from *T. longibrachiatum* is known to bind to cellulose tightly (Brooks and Ingram, 1995). The binding has also been shown to be dependent on the intensity of agitation (Kaya et al., 1994). Similar effects were seen with an intensive mass transfer reactor, where extremely high rates of hydrolysis were achieved (Gusakov et al., 1996).

SUMMARY OF THE INVENTION

Improved methods for enzymatically converting lignocellulose, for example, to ethanol, are desirable. This invention reports the use of ultrasonic treatment in a Simultaneous Saccharification and Fermentation (SSF) process to enhance the ability of cellulase to hydrolyze mixed office waste paper (MOWP), thereby reducing cellulase requirements by ⅓ to ½. SSF is a process wherein ethanologenic organisms, such as genetically engineered micro-organisms, such as *Escherichia coli* KO11 (Ingram et al., 1991) and *Klebsiella oxytoca* P2 (Ingram et al., 1995), are combined with cellulase enzymes and lignocellulose to produce ethanol. Enzyme cost is a major problem for all SSF processes.

In conducting the invention, enzyme stability is not affected and, surprisingly, continuous ultrasonic treatment results in a decrease in hydrolysis relative to discontinuous treatment. One possible explanation is that the resultant mixing does not allow the cellulase to rebind cellulose long enough for catalysis to occur. Therefore, time to allow catalysis between ultrasonic treatments is desired.

The SSF of waste office paper by *K. oxytoca* may also be "cycle dependent." Considering the inhibitory effect of ultrasound on the growth of *K. oxytoca* P2, a "recovery period" appears to be desired. With variation in the treatment schedule, such as increasing or decreasing treatment time throughout the course of fermentation, further optimization of the fermentation can be possible.

The use of ultrasound in the conversion of cellulose to ethanol represents a significant improvement in the SSF process. This is particularly true where lignin residues were used to generate the electricity required for the process. Ultrasound can be delivered in other manners as well, with liquid whistle systems, which are able to increase the water holding capacity of recycled paper (Scott and Gerber, 1995). Such a device in a piping loop can produce the desired disruption of the fine structure of cellulose, with a lower energy input.

In one embodiment, the invention comprises a method for the enzymatic degradation of lignocellulose, such as in the production of ethanol from lignocellulosic material, comprising subjecting the material to ultrasound, as in a continuously-operating ultrasonic device, cellulase enzymes, optionally an ethanologenic yeast or an ethanologenic bacterium and/or a fermentable sugar, and maintaining the mixture thus formed under conditions suitable for the production of ethanol. In an alternative embodiment, the ultrasonic device is operated discontinuously.

In a preferred embodiment, the ethanologenic organisms are organisms (particularly recombinant bacteria or yeast) which express one or more enzymes or enzyme systems which, in turn, catalyze (individually or in concert) the conversion of a sugar (e.g., xylose and/or glucose) to ethanol. Preferred ethanologenic organisms include species of Zymomonas, Erwinia, Klebsiella, Xanthomonas and Escherichia. In a highly preferred embodiment, the bacterium is K. oxytoca P2.

In another embodiment the ethanologenic yeast or ethanologenic bacterium contains enzymes that degrade lignocellulosic material, wherein the enzymes are released from the ethanologenic micro-organism by ultrasonic disruption.

DETAILED DESCRIPTION OF THE INVENTION

Figure 1:
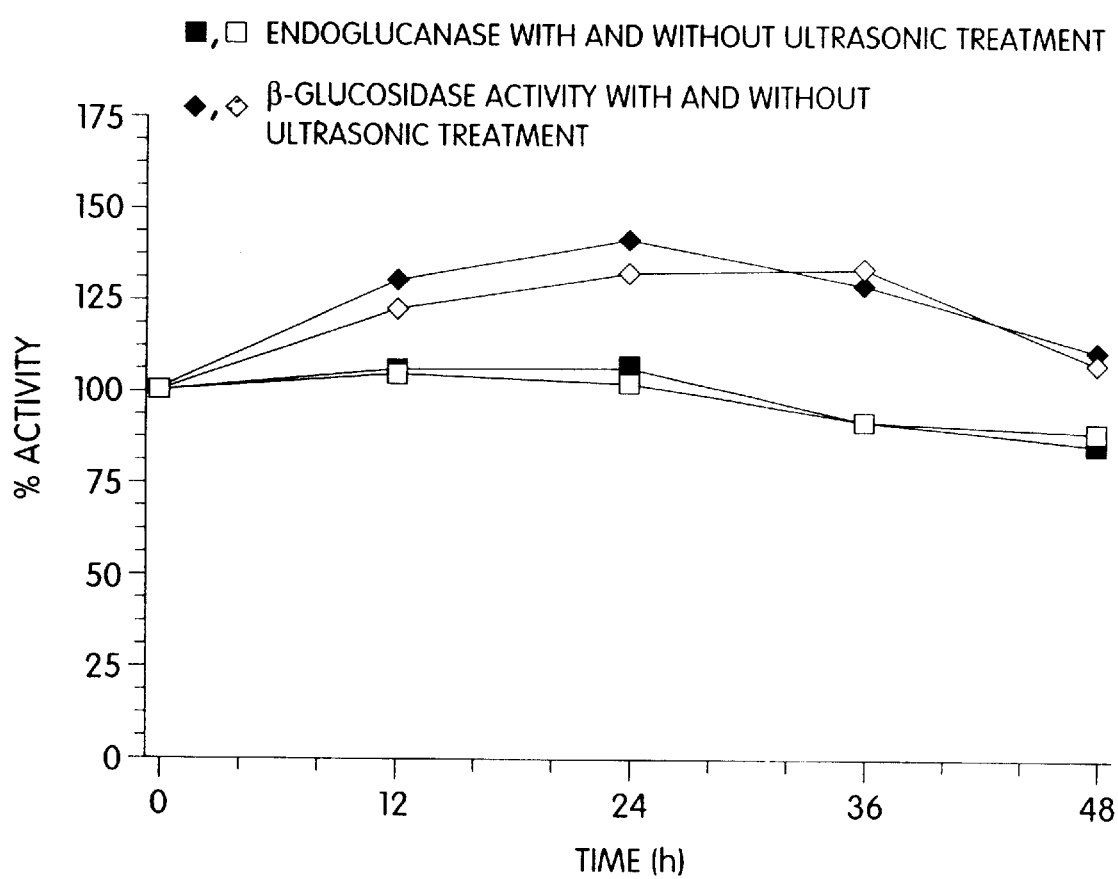
FIG. 1 shows that ultrasonic treatment did not affect the activity of the added cellulase or β-glucosidase.

As described above, the invention relates to an improved method for the enzymatic hydrolysis of lignocellulose comprising subjecting an aqueous mixture containing lignocellulose with ultrasound; and contacting the mixture with a cellulase under conditions sufficient for hydrolysis. The aqueous mixture can be subjected to the ultrasound treatment continuously or discontinuously. Typically, the ultrasound will be conducted with commercially available equipment. Examples of suitable ultrasonic probes include the RS-20 Ultrasonic Tubular Resonator and the RG-36/RS-36 Tube Resonator Systems (Telsonic USA, Bridgeport, N.J.). These ultrasonic probes may be combined with ultrasonic generators to maintain desired operating parameters, such as operating frequency and power. Examples of suitable ultrasonic generators include the RG-20 Ultrasonic-Generator and the MRG-36-150 Module-Cleaning-Generator (Telsonic USA, Bridgeport, N.J.). The ultrasound treatment may be conducted at a wide-range of frequencies, all of which exhibit similar effects. For example, the frequency can be between above 2 and 200 kHz. The duration and conditions of the ultrasonic step is selected to avoid overheating of the mixture to a temperature at which significant amounts of the enzyme(s) will be denatured. Generally, the duration of the ultrasound treatment lasts between 10 minutes and 30 minutes. Without being limited in anyway by theory, the ultrasound treatment is typically sufficient to disrupt the crystalline structure of the lignocellulosic material.

The term "continuous" treatment is defined herein to include a single treatment with ultrasound for the duration of the enzymatic hydrolysis, i.e. there are no intermediary periods between or during enzymatic hydrolysis in which there is no ultrasound. The term "discontinuous" treatment is defined herein to include multiple treatments with ultrasound between or during enzymatic hydrolysis. In yet another embodiment, the ultrasonic treatment can be a single exposure to ultrasound prior to enzymatic hydrolysis.

The lignocellulose material can be obtained from lignocellulosic waste products, such as plant residues and waste paper. Examples of suitable plant residues include stems, leaves, hulls, husks, cobs and the like, as well as wood, wood chips, wood pulp, and sawdust. Examples of paper waste include discard photocopy paper, computer printer paper, notebook paper, notepad paper, typewriter paper, and the like, as well as newspapers, magazines, cardboard, and paper-based packaging materials.

The aqueous mixture containing lignocellulose subjected to the ultrasonic treatment can further comprise a cellulase enzyme for the enzymatic hydrolysis. In yet another embodiment, the cellulase enzyme is added subsequent to the ultrasound treatment. The cellulase can be provided as a purified enzyme or can be provided by a cellulase-producing microorganism in said aqueous mixture. Cellulases, as that term is used herein, includes any enzyme that effects the hydrolysis or otherwise solubilizes cellulase (including insoluble cellulose and soluble products of cellulose). Cellulase enzymes, including purified enzyme preparations, organisms expressing the same, are known in the art. Suitable sources of cellulase include such commercial cellulase products as Spezyme™ CP, Cytolase™ M104, and Multifect™ CL (Genencor, South San Francisco, Calif.), and such organisms expressing cellulase as the recombinant bacterium of U.S. Pat. No. 5,424,202, which is incorporated herein by reference.

The conditions for cellulase hydrolysis are typically selected in consideration of the conditions suitable for the specific cellulase source, e.g, bacterial or fungal. For example, cellulase from fungal sources typically works best at temperatures between about 30° C. and 48° C. and a pH between about 4.0 and 6.0. In general, typical conditions include a temperature between about 30° C. and 60° C. and a pH between about 4.0 and 8.0.

The aqueous mixture can further advantageously comprise an ethanologenic microorganism which has the ability to convert a sugar or oligosaccharide to ethanol. Ethanologenic microorganisms are known in the art and include ethanologenic bacteria and yeast. The microorganisms are ethanologenic by virtue of their ability to express one or more enzymes which, individually or together, convert a sugar to ethanol. It is well known, for example, that Saccharomyces (such as S. cerevisiae) are employed in the conversion of glucose to ethanol. Other microorganisms that convert sugars to ethanol include species of Schizosaccharomyces (such as S. pombe), Zymomonas (including Z. mobilis), Pichia (P. stipitis), Candida (C. shehatae) and Pachysolen (P. tannophilus).

Preferred examples of ethanologenic microorganisms include ethanologenic microorganisms expressing alcohol dehydrogenase and pyruvate decarboxylase, such as can be obtained with or from Zymomonas mobilis (see U.S. Pat. Nos. 5,000,000; 5,028,539; 5,424,202; and 5,482,846, all of which are incorporated herein by reference).

In another embodiment, the ethanologenic microorganism can express xylose reductase and xylitol dehydrogenase, which convert xylose to xylulose. Xylose isomerase converts xylose to xylulose, as well. The ethanologenic microorganism can further express xylulokinase, which catalyzes the conversion of xylulose to xylulose-5-phosphate. Additional enzymes to complete the pathway can include transaldolase and transketolase. These enzymes can be obtained or derived from *Escherichia coli, Klebsiella oxytoca* and *Erwinia* species. For example, see U.S. Pat. No. 5,514,583.

It is particularly preferred to employ a microorganism which is capable of fermenting both pentoses and hexoses to ethanol, such as are obtained from preparing a recombinant organism which inherently possesses one set of enzymes and which is genetically engineered to contain a complementing set of enzymes. Examples of such microorganisms include those described in U.S. Pat. Nos. 5,000,000; 5,028,539; 5,424,202; 5,482,846; 5,514,583; and Ho et al., WO 95/13362, all of which are incorporated herein by reference. Particularly preferred microorganisms include *Klebsiella oxytoca* P2 and *Escherichia coli* KO11.

The conditions for converting sugars to ethanol are typically those described in the above referenced U.S. Patents. Generally, the temperature is between about 30° C. and 40° C. and the pH is between about 5.0 and 7.0.

It is generally advantageous to add nutrients and/or cofactors for the microorganisms and/or enzymes to optimize the enzymatic conversions. For example, xylose reductase employs NADPH and xylitol dehydrogenase employs NAD as cofactors for their respective enzymatic actions. In contrast, bacterial xylose isomerase requires no co-factor for direct conversion of xylose to xylulose. It is also desirable to add, or subject the microorganism separately to, assimilable carbon, nitrogen and sulfur sources to promote growth. Many mediums in which to grow microorganisms are well known in the art, particularly Luria broth (LB) (Luria and Delbruk, 1943).

Where the ultrasound treatment is conducted in the presence of a microorganism, the ultrasound can be conducted at a frequency and duration such that a portion of all the microorganisms present are lysed or otherwise subjected to membrane disruption. Such a method can result in a controlled release of the enzymes from the microorganisms into the surrounding medium, thereby allowing the optimization of enzymes either alone or in conjunction with commercial enzymes and reduce the overall cost of commercial enzymes.

Examples of microorganisms containing desirable enzymes include those described in U.S. Pat. No. 5,424,202 to Ingram, et al. Other microorganisms are disclosed in U.S. Pat. No. 5,028,539 to Ingram et al., U.S. Pat. No. 5,000,000 to Ingram et al., U.S. Pat. No. 5,487,989 to Fowler et al., U.S. Pat. No. 5,482,846 to Ingram et al., U.S. Pat. No. 5,554,520 to Fowler et al., U.S. Pat. No. 5,514,583 to Picataggio, et al., copending applications having U.S. Ser. No. 08/363,868 filed on Dec. 27, 1994, U.S. Ser. No. 08/475,925 filed on Jun. 7, 1995 and U.S. Ser. No. 08/218,914 filed on Mar. 28, 1994 and standard texts such as, Ausubel et al., *Current Protocols in Molecular Biology*, Wiley-Interscience, New York (1988) (hereinafter "Ausubel et al."), Sambrook et al., *Molecular Cloning: A Laboratory Manual*, Second and Third Edition, Cold Spring Harbor Laboratory Press (1989 and 1992) (hereinafter "Sambrook et al.") and Bergey's *Manual of Systematic Bacteriology*, William & Wilkins Co., Baltimore (1984) (hereinafter "Bergey's Manual") the teachings of all of which are hereby incorporated by reference in their entirety. Yet other embodiments include those described in U.S. Ser. No. 08/834,901, filed concurrently herewith by Ingram et al. and U.S. Ser. No. 08/879,005 by Ingram et al. which are incorporated herein by reference.

An example of a suitable device to deliver the ultrasound is Fisher Scientific's Model 550 Sonic Dismembrator, Telsonic Ultrasonic Tubular Resonator RS-20, Telsonic Ultrasonic-Generator RG-20, or Telsonic Tube Resonator System Series RG-36/RS-36. In one embodiment, an ultrasonic immersion horn can be used directly in the aqueous medium. Alternatively, the ultrasound can be emitted into a liquid filled vat in contact with a vat containing the aqueous medium (such as a first vat placed within a second vat, either of which can contain the aqueous medium). It may also be desirable, in a continuous system to flow the aqueous medium through a container, or vat, with the ultrasonic device which, continuously or discontinuously, emits ultrasound. In yet another embodiment, it can be desirable to control the temperature of the aqueous medium by surrounding the container, or vat, with cooling water, or other suitable heat exchange arrangement. It is within the ability of one of ordinary skill in the art to determine how to optimize the release of enzymes from microorganisms, said enzymes to be used alone or in conjunction with commercial enzymes, to achieve optimum ethanol production.

Methods and Materials

The methods and materials described below were used in carrying out the work described in the examples which follow. For convenience and ease of understanding, the methods and materials section is divided into sub-headings as follows.

Organism and Media

All fermentations of Mixed Waste Office Paper (MWOP) used *K. oxytoca* P2 as the biocatalyst. Luria broth (LB) (Luria and Delbruk, 1943) was used as the source of nutrients for all liquid and solid media. Solid media also contained 15 g/L agar and 20 g/L glucose. For the propagation of inoculum, liquid media containing 50 g/L glucose was used. Chloramphenicol (40 mg/L) was used as required for selection. Cultures were maintained on agar plates containing either 40 mg/L Cm or 600 mg/L Cm. The commercial cellulase Spezyme™ CP (Genencor, South San Francisco, Calif.), a mixture of cellulase enzymes from *Trichoderma longibrachiatum* (formerly *T. reesei*), was used. Novozyme 188, β-glucosidase from *Aspergillus niger* (Novo-Nordsk, Franklintin N.C.) was also used in saccharification experiments.

Enzyme Activity and Sugar Analysis

Endoglucanase activity was determined as previously described (Wood and Bhat, 1988). Cellulase mixtures were diluted in 50 mM citrate buffer, pH 5.2, containing 2% CMC and incubated at 35° C. Release of reducing sugars was determined by the DNS method as described (Chaplin, 1987). Cellobiase activities were determined by measuring the rate of p-nitrophenol (p-NP) release ($Abs._{410\ nm}$) from p-nitrophenyl-β-D-glucoside (p-NPG) at pH 5.2, 35° C. (Wood and Bhat, 1988). Enzyme solutions were diluted in 50 mM citrate buffer, pH 5.2, as required. One ml of diluted enzyme was added to 1 ml 2 mM p-NPG and incubated at 35° C. Reactions were terminated with the addition of 1 M $Na_2CO_3$.

Enhancement of Sugar Release from MWOP 125 g dry wt. shredded MWOP was added with 25 ml 18 N $H_2SO_4$ and 2 L $H_2O$ in a 3-liter stainless steel beaker. The slurry was allowed to react fully with the carbonate present in the paper (monitored by gas evolution). The pH was then adjusted to approximately 2.5 and autoclaved (121° C.) for 20 minutes. After overnight cooling, 125 ml 1 M sodium citrate was added and the volume was brought to 2.5 L with $H_2O$. The pH was adjusted to 5.2 and was placed in a constant temperature bath, 35° C. Mixing was done with a 750-mm Rushton-type radial flow impeller and a Ciambanco model BDC-1850 laboratory mixer. Five FPU Spezyme™ CP per gram of paper (625 FPU/2.5 L) and 50 U Novozyme 188 per liter (250 U/ 2.5 L) were also added. Units used were as reported by the manufacturer. Thymol, 0.5 g/L, and chloramphenicol, 40 mg/L was added to prevent microbial growth. Ultrasound was produced by a Telsonic 36 KHz Tube Resonator (>95% efficiency), model RS-36-30-1 with an accompanying model MRG-36-150 (150 W effective output) ultrasonic generator (Telsonic USA, Bridgeport, N.J.). The frequency was tuned automatically. Treatment cycles were controlled by an SPER Scientific 810030 timer (Fisher Scientific Co., St. Louis, Mo.). Mixing speeds were constantly adjusted to the lowest setting that would allow mixing (600–75 rpm).

Enzyme Stability

The enzyme preparations were diluted in 50 mM citrate buffer to concentrations equivalent to those used in the study of sugar release from MWOP, 250 FPU Spezyme™ CP/L and 50 U/L Novozyme 188. Solutions also contained 0.5 g/L thymol and 40 mg/L Cm to prevent microbial growth. The enzyme mixture was stirred (120 RPM) for 15 minutes to ensure complete dispersal of the enzyme. Stirring was continued for 48 hours with or without continuous exposure to ultrasound. Samples were taken at 0, 12, 24, 36, and 48 hours. Enzyme activities were assayed as described above.

Cell Viability

To 1.75 L of LB containing 50 g/L glucose and 40 mg/L Cm, $K.$ $oxytoca$ P2 was used to inoculate to an initial cell density, measured as $O.D._{550\,nm}$, of 0.5. Growth was allowed to proceed for 12 hours with or without ultrasonic treatment. Samples were taken and dilutions were made to follow cell growth at 0, ¼, ½, 1, 2, 4, 8, and 12 hours. Optical density ($O.D._{550\,nm}$) and pH were measured on each sample. Dilutions were spread on agar plates (20 g/l glucose) and incubated overnight (30° C.). Colony forming units (CFUs) were mounted as a measurement of cell viability.

Ultrastructural Effects

The change in the structure of the cellulose matrix of MWOP was investigated using a Hitachi S4000 scanning electron microscope. Samples were prepared by subjecting 2.5 L mixtures of 50 g/L MWOP in 50 mM citrate buffer, pH 5.2 and 35° C., to one hour of continuous ultrasound. Other samples were treated with cellulase for 4 hours. Control samples were taken before any treatment. All samples were dried and sputter coated with gold before being examined (Doran et al., 1994).

Cell Propagation $K.$ $oxytoca$ P2 was transferred from a stock culture (−20° C.) to agar plates with 20 g/L glucose and Cm (40 mg/l and 600 mg/l). An isolated colony was then transferred daily from the plate with 600 mg/L Cm to fresh plates containing both concentrations of Cm. Isolated colonies from plates with 40 mg/L Cm were used to inoculate flasks with LB and 50 g/L glucose. Inoculated flasks were incubated overnight at 30° C. after which they were harvested by centrifugation for further use.

SSF with Ultrasonic Treatment

Fermentations of MWOP were conducted in 14 L glass fermentation vessels (10 L working volume) using Multiferm™ fermentors models 100 and 200 (New Brunswick Sci. Co., N.J.). Stainless steel head plates were modified by removing components that extended into the broth. Head plates were sanitized with 10 g/L formaldehyde by coating all surfaces with the formaldehyde while loosely enclosed in a large plastic autoclave bag. One kg, dry weight, shredded MWOP was placed in fermentation vessels with 8 L $H_2O$ and 110 ml 18 N $H_2SO_4$. The mixture was autoclaved for one hour. After cooling, the slurry was further homogenized by vigorous mixing with a hand drill and a paint mixing attachment. After autoclaving for an additional one hour and subsequent cooling, 5 FPU Spezyme™ Cp/g MWOP, 1 L 10×LB (pH 5.0) and $H_2O$ was added to a final volume of 10 L. This solution was partially mixed by hand, using a sterilized industrial baking whisk, to disperse the enzymes and nutrients. Cells were added to an initial $O.D._{550\,nm}$ of 0.5. Ultrasonic treatments were as described above. Because of its nonhomogeneous nature, no samples were taken for an initial ethanol determination. Samples were taken at 24, 48, 72, and 96 hours.

EXAMPLE 1

Analysis of Enhanced Rates of Sugar Release

Using the methods and materials outlined above for "Enhancement of Sugar Release from MWOP," it was found that with the use of ultrasonic energy the rate of enzymatic hydrolysis was increased up to 40%. When sugar release with ultrasonic treatment 15 minutes every four hours is compared with treatment every two hours, a strong correlation between the amount of ultrasonic energy and sugar release is found. The increased rate of sugar release is due to a stimulation of enzymatic activity, not a physical or chemical hydrolysis by reactive byproducts from the sonolysis of water, as illustrated by the experiments without enzymes added. Interestingly, with continuous ultrasonic treatment, the rate of the hydrolysis goes down. Results are set forth in table format in Table 1.

TABLE 1

Effects of ultrasonic cavitation on enzymatic hydrolysis of mixed waste office paper.

| Ultrasonic treatment[a] | Number of Experiments | Energy input (W) | Glucose equivalents[b,c] (mM) | | |
|---|---|---|---|---|---|
| | | | @ 24 h | 36 h | 48 h |
| No ultrasound | 3 | 0 | 88.1 ± 6.1 | 98.3 ± 6.1 | 106.9 ± 7.8 |
| 15 min. Per 4 h | 3 | 9.37 | 96.5 ± 6.4 | 113.6 ± 8.0 | 128.3 ± 8.4 |
| 15 min. Per 2 h | 3 | 18.75 | 115.5 ± 14.3 | 133.2 ± 10.6 | 149.0 ± 11.0 |
| Continuous | 3 | 150 | 98.1 ± 2.5 | 112.5 ± 5.5 | 126.6 ± 2.1 |
| Continuous (no enzyme) | 2 | 150 | 0.67 | 0.67 | 0.58 |

[a]Ultrasonic treatments were automatically controlled to turn on and off at stated intervals.
[b]Experiments contained 5 FPU Spezyme ™CP and 10 IU Novozyme 188 /g MWOP.
[c]Based on analysis of reducing termini and assuming all are monomeric.

EXAMPLE 2

Enzyme Stability

Using the methods and materials outlined above for "Enzyme Stability," it was found that ultrasonic treatment did not affect the stability of the added cellulase or β-glucosidase, as depicted in FIG. 1. Both activities remained quite stable even with continuous exposure to ultrasound. The apparent increase in β-glucosidase may be due to the dispersal of protein aggregates in the highly concentrated, commercial, enzyme preparation.

EXAMPLE 3

Cell Viability

Figure 2A:
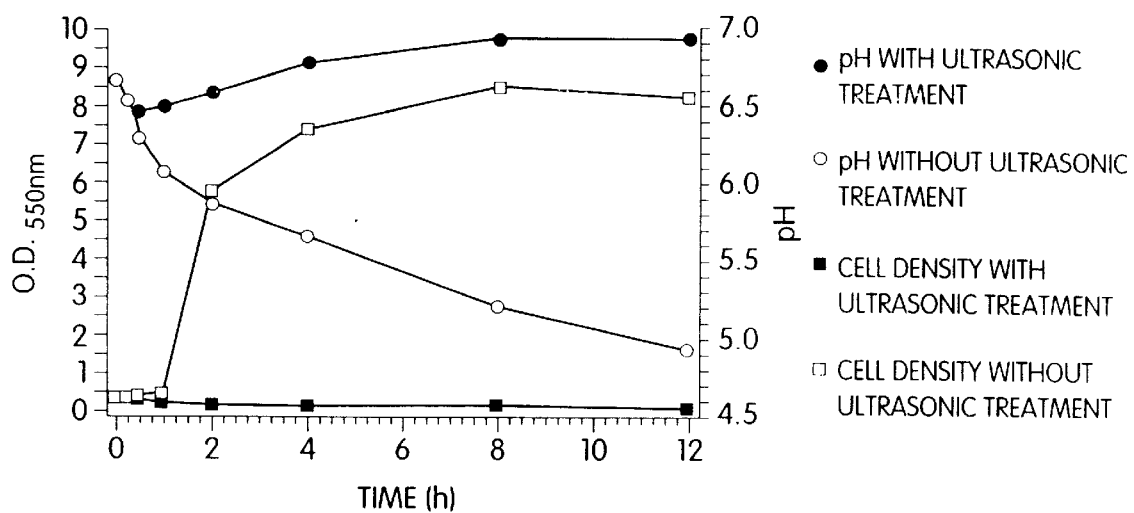
FIGS. 2A and 2B show the susceptibility of K. oxytoca P2 to ultrasonic damage.
Figure 2B:
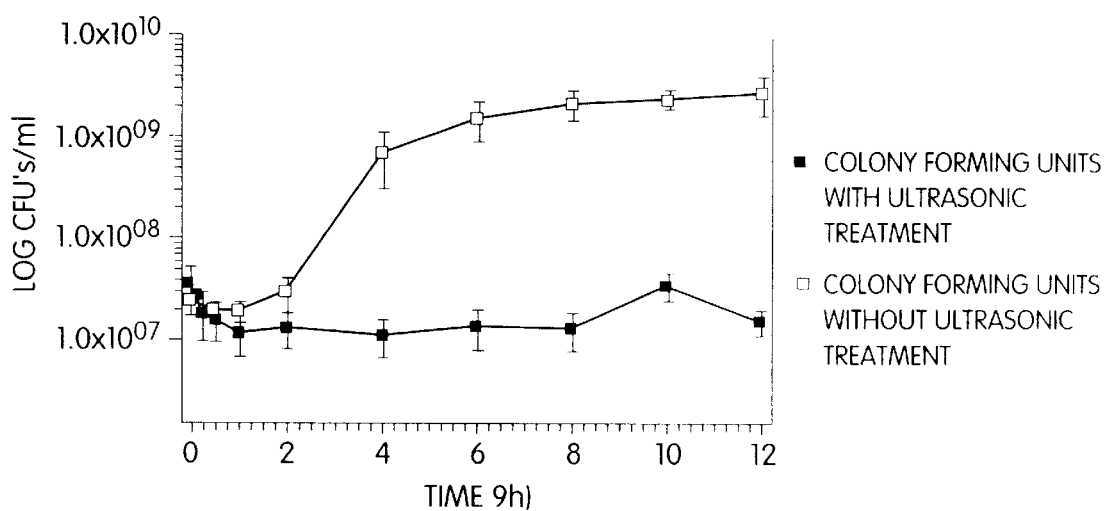

Using the methods and materials outlined above for "Cell Viability," it was found that ultrasonic treatment appeared to be nonlethal, but was inhibitory to growth, as shown in FIGS. 2A and 2B. This observation may be due in part to an induction of an SOS response by the cells. This was further supported by the observations of pH, which slightly increased (pH 6.9 from an initial pH 6.7). Additionally, it was observed that the relative turbidity of the broth had little change throughout the exposure to ultrasound. Meanwhile, without ultrasonic treatment, a classical growth curve was observed.

EXAMPLE 4

Effects on SSF

Using the methods and materials outlined above for "SSF with Ultrasonic Treatment," the combination of *K. oxytoca* P2 with ultrasonic treatment resulted in as much as a 15% increase in ethanol yields. Ethanol production from waste office paper treated with ultrasound and *K. oxytoca* P2 is summarized in Table 2. As might be expected from the inhibition of cell growth, increased ultrasonic treatment results in reduced ethanol production. Treatment every two hours may not be significantly different from treatment every four hours, however, a statistically significant difference between ultrasonic treatment every four hours and no treatment was found.

TABLE 2

Effects of ultrasonic treatment on ethanol production in SSF of MWOP using K. oxytoca P2 as the biocatalyst

| Ultrasonic treatment | Replicates | [Enzyme]$^a$ (FPU/g MWOP) | [Ethanol] (g/L) 24 h | 48 h | 72 h | 96 h | Yield$^{b,c}$ (GE/g Cellulose) |
|---|---|---|---|---|---|---|---|
| None | 2 | 10 | 15.7 | 27.3 | 33.5 | 35.3 | 0.39 |
| None | 4 | 5 | 9.5 ± 2.3 | 19.0 ± 2.7 | 25.7 ± 2.5 | 29.4 ± 2.9 | 0.33 |
| 15 min. Per 4 h (9.37 W) | 5 | 5 | 14.3 ± 2.0 | 26.1 ± 1.3 | 31.3 ± 1.3 | 34.0 ± 1.9 | 0.38 |
| 15 min per 2 h (18.75 W) | 2 | 5 | 13.4 | 23.4 | 28.8 | 31.4 | 0.35 |
| Continuous (150 W) | 2 | S | 10.2 | 11.2 | 11.3 | 11.3 | 0.13 |

$^a$Enzyme added was Spezyme ™CP cellulase (Genencor, Inc. South San Francisco, CA), Enzyme activity was determined by the manufacturer.
$^b$MWOP contains approximately 90% Cellulose (Brooks and Ingram, 1995.)
$^c$Theoretical maximum yield is 0.568 g ethanol per g cellulose.
$^d$Unpaired t-tests show these results to be statistically different (p-0.0224).

Bibliography

Allison, D. G., A. D'Emanuele, and A. R. Williams. "The effect of ultrasound on *Escherichia coli* viability" 1996. *J. Basic Microbiol.* 36(1):3–11.

Atchley, A. A., and L. A. Crum. "Chapter 1: Acoustic cavitation and bubble dynamics" *Ultrasound: Its Chemical, Physical, and Biological Effects.* K. S. Suslick ed. VCH, New York, N.Y. 1988.

Ausubel, F. M., R. Brent, R. E. Kingston, D. D. More, J. G. Seidman, J. A. Smith, and K. Struhl. *Current Protocols in Molecular Biology.* Green Publishing and Wiley Interscience, New York, N.Y. 1996

Boudjouk, P. "Chapter 5. Heterogeneous sonochemistry" *Ultrasound: Its Chemical, Physical, and Biological Effects.* K. S. Suslick ed. VCH, New York, N.Y. 1988.

Brooks, T. A. and L. O. Ingram. "Conversion of mixed office paper to ethanol by genetically engineered *Klebsiella oxytoca* strain P2" 1995. *Biotechnol. Prog.* 11(6): 619–625

Doran, J. B., H. C. Aldrich, and L. O. Ingram. "Saccharification and fermentation of sugar canebagasse by *Klebsiella oxytoca* P2 containing chromosomally integrated genes encoding the *Zymomonas mobilis* ethanol pathway" 1994. *Biotechnol. Bioeng.* 44:240–247.

Gusakov, A. V., A. P. Sinitsyn, I. Y. Davydkin, V. Y. Davydkin. and O. V. Protas. "Enhancement of enzymatic cellulose hydrolysis using a novel type of bioreactor with intensive stirring induced by electromagnetic field" 1996. *Appl. Biochem. Biotechnol.* 56:141–153.

Hohmann, N., and C. M Rendleman. *Emerging Technologies in Ethanol Production* USDA Ag. Info. Bulletin no. 663. U.S. Department of Agriculture: Washington D.C. January 1993.

Ingram, L. O. and J. B. Doran. "Conversion of cellulosic materials to ethanol" 1995. *FEMS Microbiol. Rev.* 16:235–241

Ingram, L. O., D. S. Beall, G. F. H. Burchardt, W. V. Guimaraes, K. Ohta, B. E. Wood, and K. T. Shanmugam. "Ethanol production by recombinant hosts" 1995. U.S. Pat. No.5,424,202.

Ingram, L. O., T. Conway, and F. Altertghum. "Ethanol production by *Escherichia coli* strains co-expressing Zymomonas pds and adh genes" 1991. U.S. Pat. No. 5,000,000.

Kaya, F., J. A. Heitmann, Jr., and T. W. Joyce. "Cellulase binding to cellulose fibers in high shear fields" 1994. *J. Biotech.* 36:1–10.

Leeman, S., and P. W. Vaughn. "Cavitation phenomena" *Current Trends in Sonochemisty.* G. J. Price ed. Royal Society of Chemistry Special Publication No. 116. Royal Society of Chemisty: Cambridge U.K. 1992.

Nazhad, M. M., L. P. Ramos, L. Paszner, and J. N. Sadler. "Structural constraints affecting the initial enzymatic hydrolysis of recycled paper" 1995. *Enz. Microb. Tech.* 17:68–74.

Norman, J. C., N. J. Sell, and M. Danelski. "Deinking laser-print paper using ultrasound" 1994. *TAPPI J.* 77:151–158.

Price, G. J. "Introduction to sonochemistry" *Current Trends in Sonochemisty.* G. J. Price ed. Royal Society of Chemistry Special Publication No. 116. Royal Society of Chemistry:Cambridge U.K. 1992.

Scott, W. E. and P. Gerber. "Using ultrasound to deink xerographic waste" 1995. *TAPPI J.* 78:125–130.

Sell, N. J., J. C. Norman, and D. Jayaprakash. "Deinking secondary fiber using ultrasound" 1995. *Progress in Paper Recycling.* August p.28–34.

Sheehan, J. J. "Chapter 1. Bioconversion for production of renewable transportation fuels in the United States: a strategic perspective" *Enzymatic Conversion of Biomass for Fuels Production.* Himmel, M. E.; Baker, J. O.; Overend, R. P. eds. ACS Symposium Series 566. American Chemical Society: Washington D.C. 1993.

Shoh, A. "Chapter 3. Industrial applications of ultrasound" *Ultrasound:Its Chemical, Physical, and Biological Effects.* K. S. Suslick ed. VCH, New York, N.Y. 1988.

Suslick, K. S. "Chapter 4. Homogeneous sonochemistry" *Ultrasound:Its Chemical, Physical, and Biological Effects.* K. S. Suslick ed. VCH, New York, N.Y. 1988. 123–146.

Suslick, K. S. "Sonochemistry" 1990. *Science.* 247:1439–1441.

Suslick, K. S. "The Chemical Effects of Ultrasound" 1989. *Scientific American.* February p. 80–86.

Volmer, A. C., I. R. S. Maken and E. C. Everbach. "Induction of the heat shock response in *Escherichia coli* by the effects of acoustic cavitation from Ultrasound" Abstr. I-85, p. 317. Abstr. 96th Annu. Meet. Am. Soc. Microbiol. American Society for Microbiology, Washington D.C. 1996.

Wang, D., M. Sakakibara, N. Kaoyuki, and K. Suzuki. "Ultrasound enhanced lactose hydrolysis in milk fermentation with *Lactobacillus bulgaricus*" 1996. *J. Chem Tech. Biotechnol.* 65:86–92.

Wood, T. M. and K. M. Bhat. "Methods for measuring cellulase activities" 1988. *Methods in Enzymology.* 160:87–144.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for producing ethanol from lignocellulose comprising discontinuously treating an aqueous mixture containing lignocellulose, a cellulase and an ethanologenic microorganism with ultrasound under conditions sufficient for hydrolysis of said lignocellulose to occur, to thereby produce ethanol.

2. The method according to claim 1 wherein said cellulase is provided by a cellulase-producing microorganism in said aqueous mixture.

3. The method according to claim 1 wherein said aqueous mixture is treated with ultrasound at a frequency of between about 2 and 200 kHz.

4. The method according to claim 1 wherein said ethanologenic microorganism is an ethanologenic bacteria or yeast.

5. The method according to claim 4 wherein said ethanologenic microorganism is a bacteria or yeast which expresses one or more enzymes which, individually or together, convert a sugar to ethanol.

6. The method according to claim 4 wherein said ethanologenic microorganism expresses enzymes which, individually or together, convert pentose and hexose to ethanol.

7. The method according to claim 4 wherein said ethanologenic microorganism expresses alcohol dehydrogenase and pyruvate decarboxylase.

8. The method according to claim 7 wherein said alcohol dehydrogenase and pyruvate decarboxylase are from *Zymomonas mobilis.*

9. The method according to claim 4 wherein said ethanologenic microorganism expresses xylose isomerase, xylulokinase, transaldolase, and transketolase.

10. The method according to claim 9 wherein said xylose isomerase, xylulokinase, transaldolase, and transketolase are from *Escherichia coli.*

11. The method according to claim 9 wherein said xylose isomerase, xylulokinase, transaldolase, and transketolase are from *Klebsiella oxytoca.*

12. The method according to claim 9 wherein said xylose isomerase, xylulokinase, transaldolase, and transketolase are from Erwinia species.

13. The method according to claim 4 wherein said ethanologenic microorganism expresses alcohol dehydrogenase, pyruvate decarboxylase, xylose isomerase, xylulokinase, transaldolase, and transketolase.

14. The method according to claim 13 wherein said ethanologenic microorganism is a recombinant microorganism expressing *Zymomonas mobilis* alcohol dehydrogenase and pyruvate decarboxylase wherein said microorganism is selected from the group consisting of *Escherichia coli, Klebsiella oxytoca,* and Erwinia species.

15. The method according to claim 14 wherein said ethanologenic microorganism is *Klebsiella oxytoca* P2.

16. The method according to claim 14, wherein said ethanologenic microorganism is *Escherichia coli* KO11.

* * * * *